United States Patent
Franklin et al.

(10) Patent No.: US 10,413,439 B2
(45) Date of Patent: Sep. 17, 2019

(54) WEARABLE GARMENT THAT RESTRICTS RANGE OF MOTION OF LIMBS

(71) Applicants: Jacky L. Franklin, Elmwood, TN (US); T. Hank Robinson, Omaha, NE (US)

(72) Inventors: Jacky L. Franklin, Elmwood, TN (US); T. Hank Robinson, Omaha, NE (US)

( * ) Notice: Subject to any disclaimer, the term of this patent is extended or adjusted under 35 U.S.C. 154(b) by 0 days.

(21) Appl. No.: 15/843,132

(22) Filed: Dec. 15, 2017

(65) Prior Publication Data
US 2019/0183669 A1 Jun. 20, 2019

(51) Int. Cl.
*A61F 5/37* (2006.01)
*A41D 13/02* (2006.01)

(52) U.S. Cl.
CPC ............ *A61F 5/3723* (2013.01); *A41D 13/02* (2013.01); *A41D 2300/322* (2013.01)

(58) Field of Classification Search
CPC .... A41D 27/10; A41D 13/06; A41D 13/1236; A41D 13/1245; A41D 13/1263; A41D 13/02; A61F 5/373; A61F 5/3723; A61F 5/3732; A61F 5/3746; A61F 5/3753; A61F 5/37; A61F 5/3715
USPC ..... 2/71–72, 79, 86, 88, 114, 125, 212–213, 2/69, 69.5, 105, 214; 128/873–874
See application file for complete search history.

(56) References Cited

U.S. PATENT DOCUMENTS

| | | | |
|---|---|---|---|
| 3,502,073 A | | 3/1970 | Stanley |
| 3,862,877 A | * | 1/1975 | Camden ................. D04H 5/04 428/111 |
| 5,176,600 A | * | 1/1993 | Wilkinson ......... A41D 13/0015 482/105 |
| 5,196,240 A | * | 3/1993 | Stockwell ......... A41D 13/0005 2/82 |

(Continued)

FOREIGN PATENT DOCUMENTS

| | | | |
|---|---|---|---|
| JP | 2004-344563 A | * | 9/2004 |
| JP | 2004-344563 A | * | 9/2004 |

OTHER PUBLICATIONS https://www.sleepingbaby.com/pages/how-the-zipadeezip-works.
International Search Report and Written Opinion dated Mar. 5, 2019 for PCT/US2018/065639.

*Primary Examiner* — Kari K Rodriquez
*Assistant Examiner* — Camtu T Nguyen
(74) *Attorney, Agent, or Firm* — Suiter Swantz pc llo (57) ABSTRACT

A garment for restricting the range of motion of a wearer can include a body assembly with one or more garment forming portions configured to form a first side and a second side. The first side and the second side can be removably joined by at least one fastener. The garment further includes first and second sleeves coupled to the body assembly at first and second armpit areas, respectively. Each of the sleeves can be securely attached to the body assembly by first and second attachment devices, respectively. Each of the first attachment device and the second attachment device can extend vertically from the respective armpit area toward a distal end (Continued)

of the respective sleeve. The garment also includes first and second leg portions that can be joined by a third attachment device extending vertically from an inseam toward a distal end of the first and second leg portions.

8 Claims, 8 Drawing Sheets

(56) References Cited

U.S. PATENT DOCUMENTS

| | | | |
|---|---|---|---|
| 5,713,373 A * | 2/1998 | Argentino | A61F 5/37 128/869 |
| 6,024,091 A | 2/2000 | Bennett | |
| 6,212,684 B1 | 4/2001 | Waheed | |
| 6,604,245 B1 * | 8/2003 | Kinnier | A41D 13/00 2/227 |
| 6,651,258 B2 * | 11/2003 | Pelensky | A41B 13/005 2/227 |
| 7,117,538 B2 * | 10/2006 | Bosne | A41D 3/00 2/93 |
| 7,827,619 B1 * | 11/2010 | Steinberg | A41D 11/00 2/114 |
| 7,874,019 B2 | 1/2011 | Woolcott et al. | |
| 7,985,144 B1 | 7/2011 | Gonzales | |
| 8,215,313 B1 * | 7/2012 | Waltz | A61F 5/3715 128/849 |
| 8,230,520 B2 * | 7/2012 | Riondato | A41D 1/084 2/275 |
| 8,479,315 B2 * | 7/2013 | Kelling | A41D 15/04 2/69 |
| 9,061,195 B1 * | 6/2015 | Collins | A63B 69/0059 |
| 2003/0145636 A1 | 8/2003 | Nykoluk | |
| 2008/0053464 A1 | 3/2008 | Wilson | |
| 2010/0081982 A1 * | 4/2010 | Takahashi | A61L 15/585 602/41 |

* cited by examiner

WEARABLE GARMENT THAT RESTRICTS RANGE OF MOTION OF LIMBS

BACKGROUND

Restraints are utilized by law enforcement officers and other institutional employees to control uncooperative or violent prisoners and patients.

SUMMARY

A garment for restricting the range of motion of a wearer is disclosed. In an embodiment, the garment includes a body assembly with one or more garment forming portions configured to form a first side and a second side. The first side and the second side can be removably joined by at least one fastener. The garment further includes first and second sleeves coupled to the body assembly at first and second armpit areas, respectively. Each of the sleeves can be securely attached to the body assembly by first and second attachment devices, respectively. Each of the first attachment device and the second attachment device can extend vertically from the respective armpit area toward a distal end of the respective sleeve. The garment also includes first and second leg portions that can be joined by a third attachment device extending vertically from an inseam toward a distal end of the first and second leg portions.

In another embodiment, a garment for restricting the range of motion of a wearer includes an upper jacket portion having a first sleeve and a second sleeve coupled to a torso area. The sleeves are coupled to the torso area at first and second armpit areas, respectively. Each of the sleeves is securely attached to the torso area by a first attachment device and a second attachment device, respectively. Each of the first attachment device and the second attachment device can extend vertically from the respective armpit area toward a distal end of the respective sleeve. The garment also includes a lower pants portion including first and second leg portions coupled to a waist area. The first leg portion and the second leg portion can be joined by a third attachment device extending vertically from an inseam and toward a distal end of the leg portions. The upper jacket portion and the lower pants portion can be removably coupled at the waist area by at least one fastener.

In another embodiment, a garment for restricting the range of motion of a wearer includes a body assembly, the body assembly having one or more garment forming portions configured to form an upper jacket portion and a lower pants portion coupled at a waist. The garment further includes a first sleeve coupled to the body assembly at a first armpit area. The first sleeve can be securely attached to the body assembly by a first attachment device extending vertically from the first armpit area and terminating near a distal end of the first sleeve. The garment also includes a second sleeve coupled to the body assembly at a second armpit area. The second sleeve can be securely attached to the body assembly by a second attachment device extending vertically from the second armpit area and terminating near a distal end of the second sleeve. The garment further includes a first leg portion and a second leg portion, each of the first leg portion and the second leg portion being coupled to the body assembly at an inseam. The first leg portion and the second leg portion can be joined by a third attachment device extending vertically from the inseam and terminating near a distal end of the first and second leg portions. The garment also includes at least one fastener configured to extend from a neck area of the upper jacket portion to a portion of the lower pants portion.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Law enforcement officers, prison officers, and other institutional employees frequently face risks that can affect their health, safety, and well-being. These persons are at increased risk of workplace injury due to inadequate management systems and processes for dealing with noncompliant prisoners or patients. Existing wearable restraints for prisoners or patients (e.g., strait jackets, handcuffs, shackles, etc.) are often cumbersome to employ, unnecessarily uncomfortable for the wearer, and overly restrictive. Other non-wearable restraints (e.g., restraint chairs, restraint benches, restraint beds, etc.) are often costly, difficult to use, and have limitations like those of wearable restraints. These existing restraints also restrict autonomous activity. For example, the excessive restriction of these restraints renders them difficult to utilize in a workplace or classroom setting. Wearers of existing restraints are often unable to perform even the most basic activities without assistance (e.g., eating, drinking, etc.). Further, the use of existing restraints creates bias and stigmatization against the wearer in a courtroom setting (e.g., in front of a jury). Additionally, there is a need for a pre-deployed wearable restraint that acts as baseline for security control to which additional restraints can be added as needed.

A garment is described for restricting the range of motion of a wearer. The garment includes a body assembly with one or more garment forming portions configured to form a first side and a second side. The first side and the second side can be removably joined by at least one fastener. The garment further includes first and second sleeves coupled to the body assembly at first and second armpit areas, respectively. Each of the sleeves can be securely attached to the body assembly by first and second attachment devices, respectively. Each of the first attachment device and the second attachment device can extend vertically from the respective armpit area toward a distal end of the respective sleeve. The garment also includes first and second leg portions that can be joined by a third attachment device extending vertically from an inseam toward a distal end of the first and second leg portions.

Example Implementations

Referring generally to FIGS. 1 through 8, a motion restriction garment 100 is described that is configured to restrict the range of limb motion of a wearer 102. The motion restriction garment 100 includes a body assembly 104 coupled with first and second sleeves 106A, 106B, and first and second leg portions 108A, 108B. The sleeves 106A, 106B and/or leg portions 108A, 108B are configured to restrict the range of motion of the wearer 102.

Figure 1:
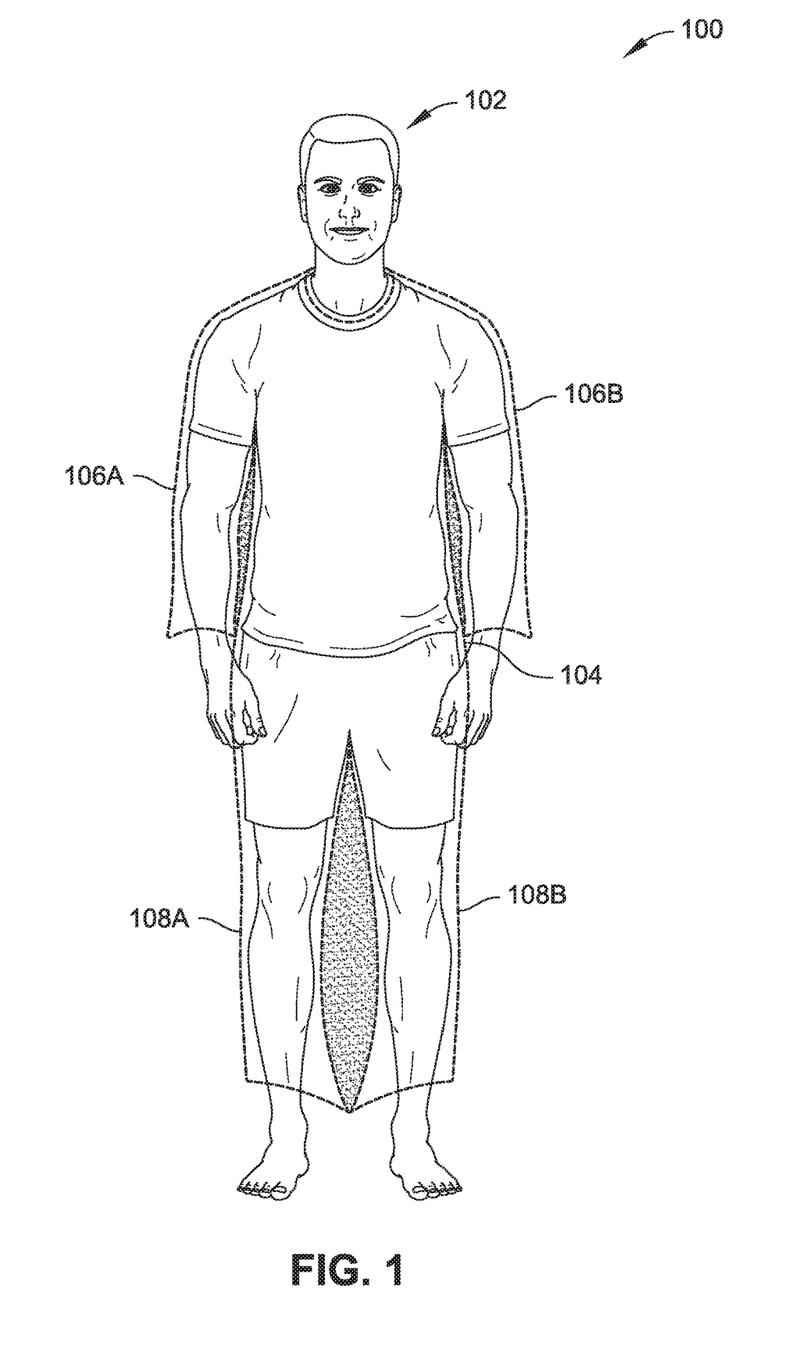
FIG. 1 is a front view illustrating a motion restriction garment in accordance with an example embodiment of the present disclosure.
Figure 2A:
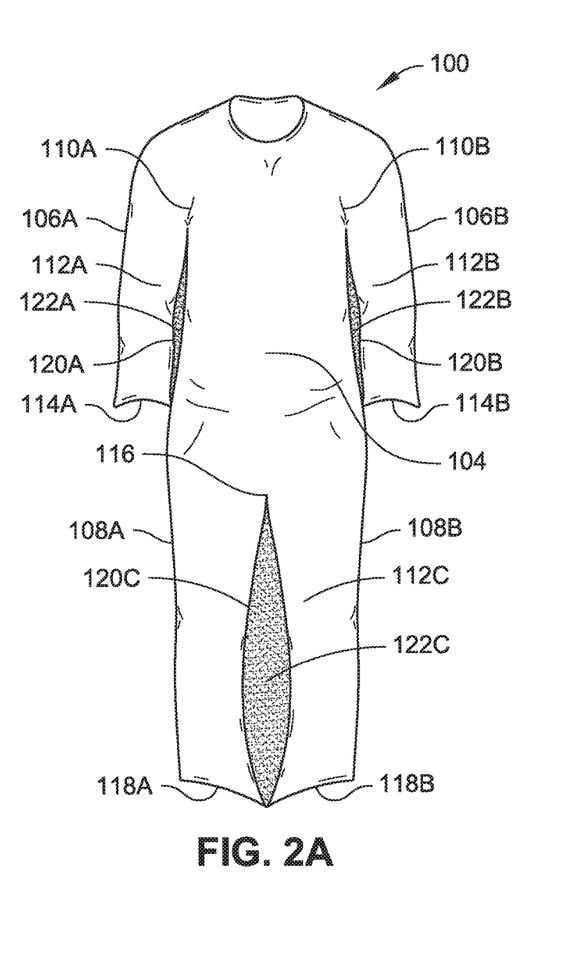
FIG. 2A is another front view illustrating a motion restriction garment in accordance with an example embodiment of the present disclosure.
Figure 2B:
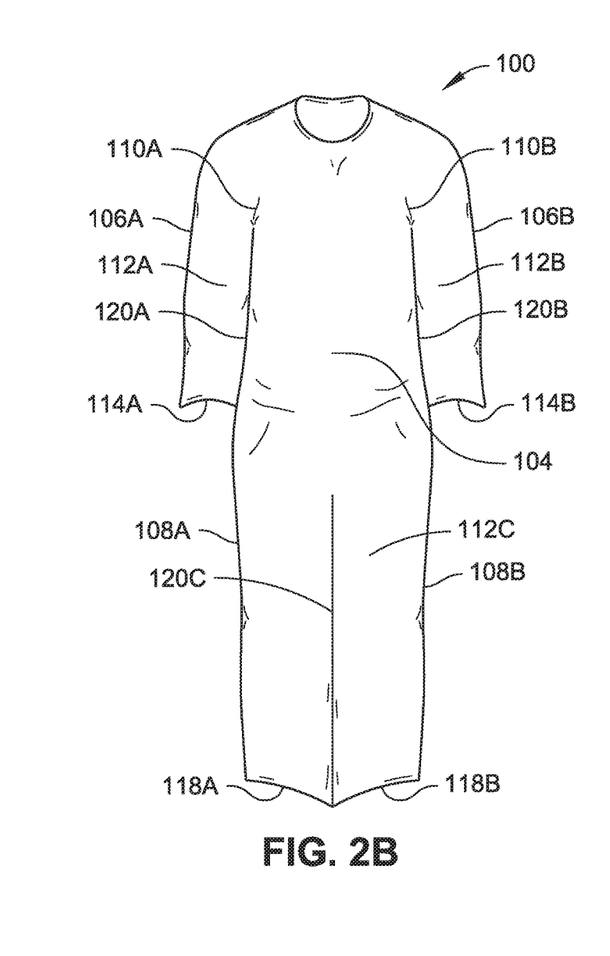
FIG. 2B is another front view illustrating a motion restriction garment in accordance with an example embodiment of the present disclosure.

Referring now to FIGS. 2A and 2B, the first and second sleeves 106A, 106B are coupled to the body assembly 104 at first and second armpit areas 110A, 110B, respectively. The leg portions 108A, 108B are coupled to the body assembly 104 at an inseam. In embodiments, the sleeves 106A, 106B and/or the leg portions 108A, 108B are configured to restrict the range of motion of the wearer 102. The first sleeve 106A and the second sleeve 106B can be securely attached to the body assembly 104 by attachment devices, for example, first and second attachment devices 112A, 112B, respectively. In embodiments, the attachment devices 112A, 112B can include, but are not necessarily limited to: seams, zippers, a fastener material (e.g., Velcro® available from Velcro Companies, London, UK), buttons, snaps, buckles, other similar fasteners, and so forth. In embodiments, each of the first attachment device 112A and the second attachment device 112B extend vertically from the respective armpit area 110A, 110B toward a distal end 114A, 114B of the respective sleeve 106A, 106B. In some embodiments, the first and second attachment devices 112A, 112B are configured to extend at least ½ of the length of the first and second sleeves 106A, 106B, respectively. In some embodiments, the attachment devices 112A, 112B are configured to extend from approximately ½ of the length of the sleeve 106A, 106B to approximately the entirety of the length of the sleeve 106A, 106B. In a specific embodiment, the attachment devices 112A, 112B are configured to terminate near the distal ends 114A, 114B of sleeves 106A, 106B, respectively (e.g., near the cuff or opening). The length of the attachment devices 112A, 112B can be selected based on the desired range of motion of the wearer 102. For example, if a greater range of motion is desired, a shorter attachment device 112A, 112B can be utilized. This allows for the wearer 102 to retain a desired range of motion (e.g., enabling the wearer 102 to retain use their hands without allowing the wearer 102 to remove the garment 100).

Still referring to FIGS. 2A and 2B, leg portions 108A, 108B are coupled to the body assembly 104 at an inseam 114. In some embodiments, the first leg portion 108A can be joined to the second leg portion 108B by an attachment device (e.g., third attachment device 112C). In embodiments, the attachment device 112C can include, but is not necessarily limited to: seams, zippers, a fastener material (e.g., Velcro® available from Velcro Companies, London, UK), buttons, snaps, buckles, other similar fasteners, and so forth. In embodiments, the third attachment device 112C is configured to extend vertically from the inseam 114 toward a distal end 118A, 118B of the leg portions 108A, 108B. In some embodiments, the first and second attachment devices 112A, 112B are configured to extend at least ½ of the length of the first and second sleeves 106A, 106B, respectively. In some embodiments, the attachment device 112C is configured to extend from approximately ½ of the length of the leg portions 108A, 108B to approximately the entirety of the length of the leg portion 108A, 108B. In a specific embodiment, the attachment device 112C is configured to terminate near the distal ends 118A, 118B of the leg portions 108A, 108B (e.g., near the cuff or opening). The length of the attachment device 112C can be selected based on the desired range of motion of the wearer 102. For example, if a greater range of motion is desired, a shorter attachment device 112C can be utilized. This allows for the wearer 102 to retain a desired range of motion (e.g., enabling the wearer 102 shuffle or walk, while restricting the ability of the wearer 102 to run or remove the garment 100).

In embodiments, the attachment devices 112A, 112B, 112C can be configured in a variety of ways. In some embodiments, the attachment devices can be configured to define a portion of textile material between the sleeves 106A, 106B and the body assembly 104 and/or between the leg portions 108A, 108B (e.g., as described with reference to FIG. 2A). For example, the first attachment device 112A can include a first seam 120A defining a first section of textile material 122A positioned between the first sleeve 106A and body assembly 104, and the second attachment device can include a second seam 120B defining a second section of textile material 122B positioned between the second sleeve 106B and body assembly 104. The third attachment device 112C can include a third seam 120C defining a third section of textile material 122C positioned between the first leg portion 108A and the second leg portion 108B. It is contemplated that the sections of textile material 122A, 122B, 122C can be integral to the garment 100, or formed from separate pieces of material. In other embodiments, the sleeves 106A, 106B can be securely attached directly to the body assembly, and the leg portion 108A can be securely attached directly to 108B (e.g., as described with reference to FIG. 2B. For example, seams 120A, 120B can be configured to extend vertically (e.g., straight seams) from the armpit area 110A, 110B and directly couple the sleeves 106A, 106B to the body assembly 104. Similarly, seam 120C can be configured to extend vertically from the inseam 116 (e.g., straight seam) and directly couple leg portion 108A to leg portion 108B.

Figure 3:
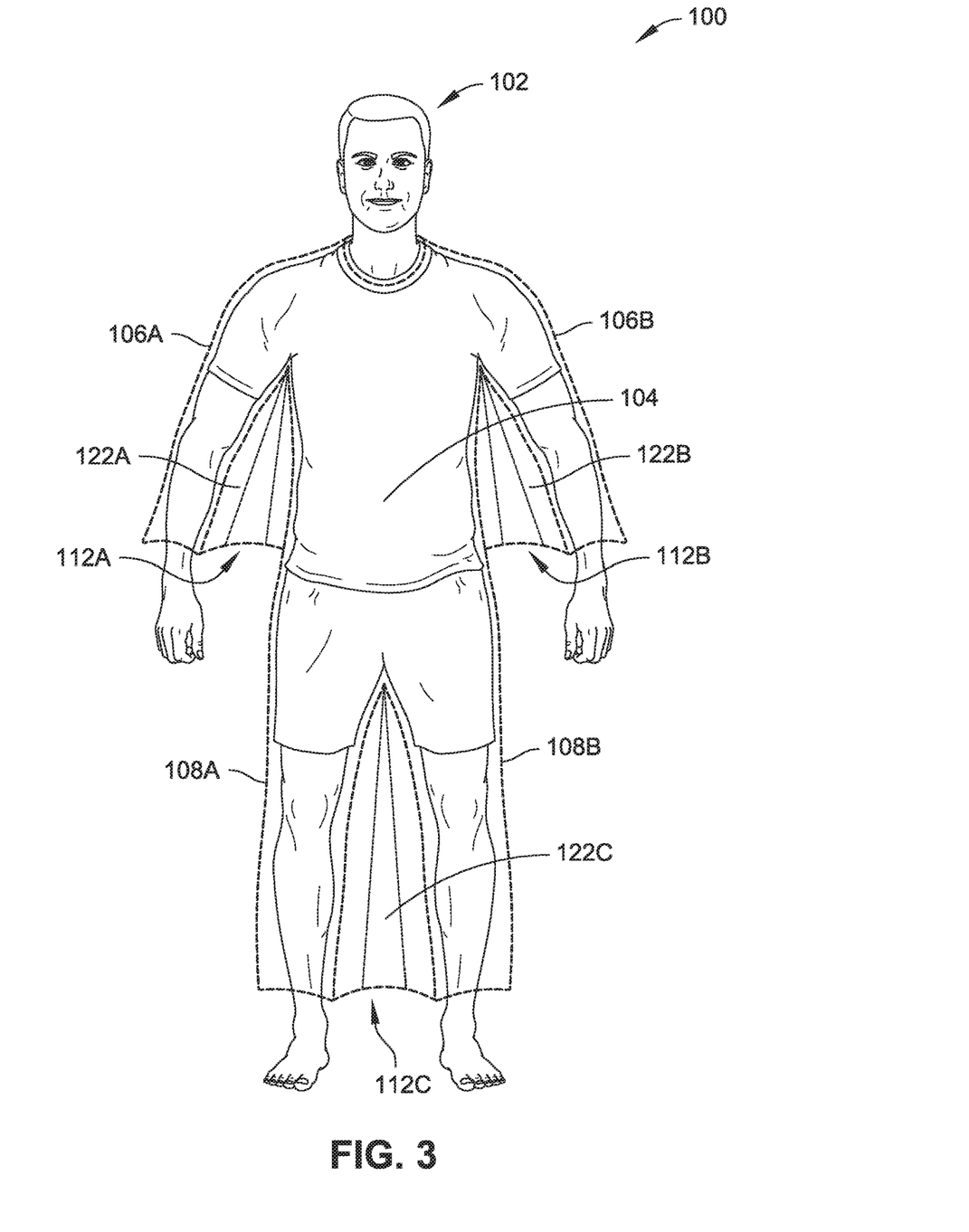
FIG. 3 is a front view illustrating a motion restriction garment including adjustable attachment devices at the sleeves and leg portions in accordance with an example embodiment of the present disclosure.

Referring now to FIG. 3, the attachment devices 112A, 112B, 112C can include adjustable fasteners configured to adjust the distance between the sleeves 106A, 106B and the body assembly 104, and or the distance between the leg portions 108A, 108B. For example, the attachment device 112A, 112B can include a zipper with a single female end disposed on the body assembly 104, and a male end disposed on the sleeve 106A, 106B and configured to mate with the corresponding female end. Textile material section 122A, 122B can be disposed between the body assembly 104 and the sleeve 106A, 106B, and can include a plurality of folds (e.g., an accordion fold configuration). Each fold can further include a male zipper end configured to mate with the corresponding female end disposed on the body assembly. The distance between the sleeves 106A, 106B and the body assembly 104 can be adjusted by mating the female zipper end to the male zipper end disposed on a selected fold, increasing or decreasing the width of the textile material section 122A, 122B. Similarly, attachment device 112C can include a zipper with a single female end disposed on either the first or second leg portion 108A, 108B, and a male end disposed on the opposing leg portion 108A, 108B and configured to mate with the corresponding female end. Textile material section 122C can be disposed between the leg portions 108A, 108B, and can include a plurality of folds (e.g., an accordion fold configuration). Each fold can further include a male zipper end configured to mate with the corresponding female end disposed on the body assembly. The distance between the first leg portion 108A and the second leg portion 108B can be adjusted by mating the female zipper end to the male zipper end disposed on a selected fold, increasing or decreasing the width of the textile material section 122C. The attachment device 112A, 112B, 112C can further include a locking device (e.g., snap, button, zip-tie, etc.) configured to retain the attachment device 112A, 112A, 112C in a selected orientation. For example, the zippers described above can include a locking device configured to retain the zipper in a zipped orientation.

Figure 4:
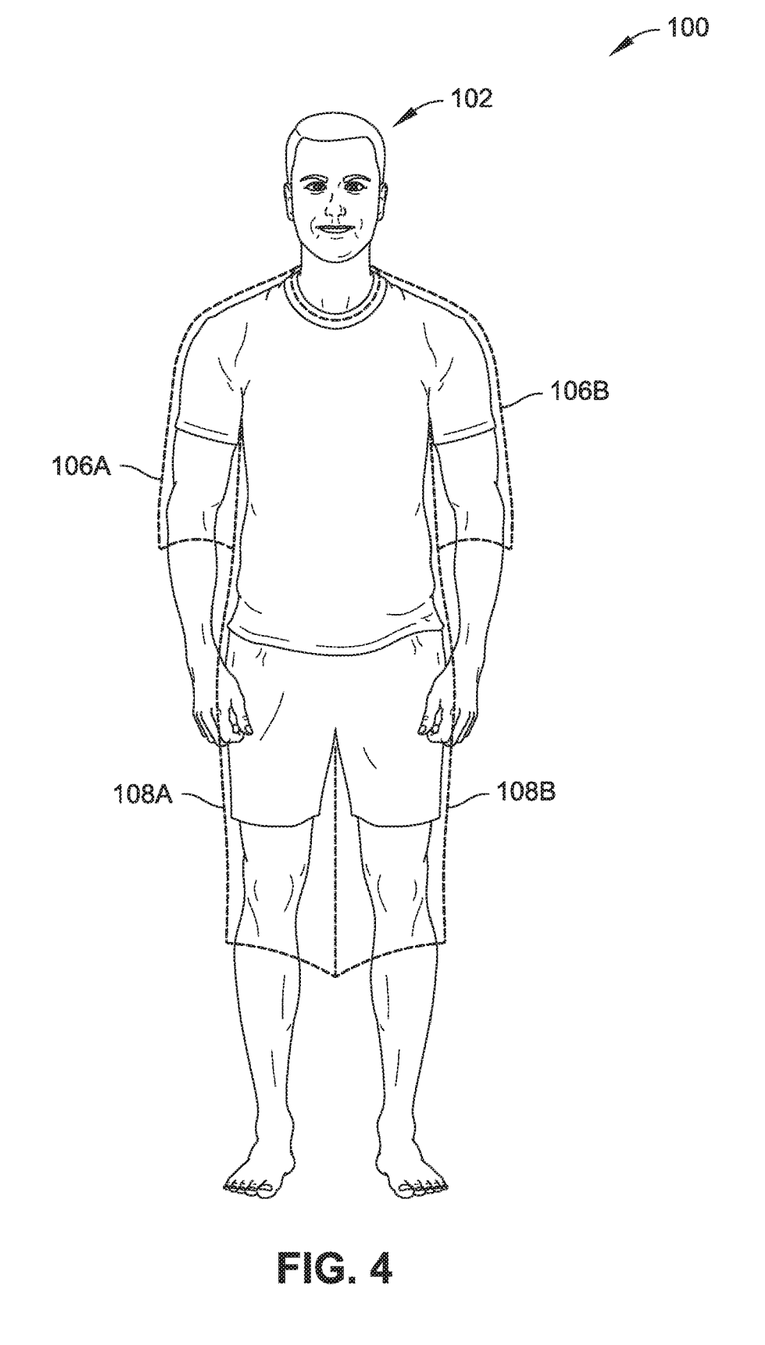
FIG. 4 is another front view illustrating a motion restriction garment in accordance with an example embodiment of the present disclosure.
Figure 5:
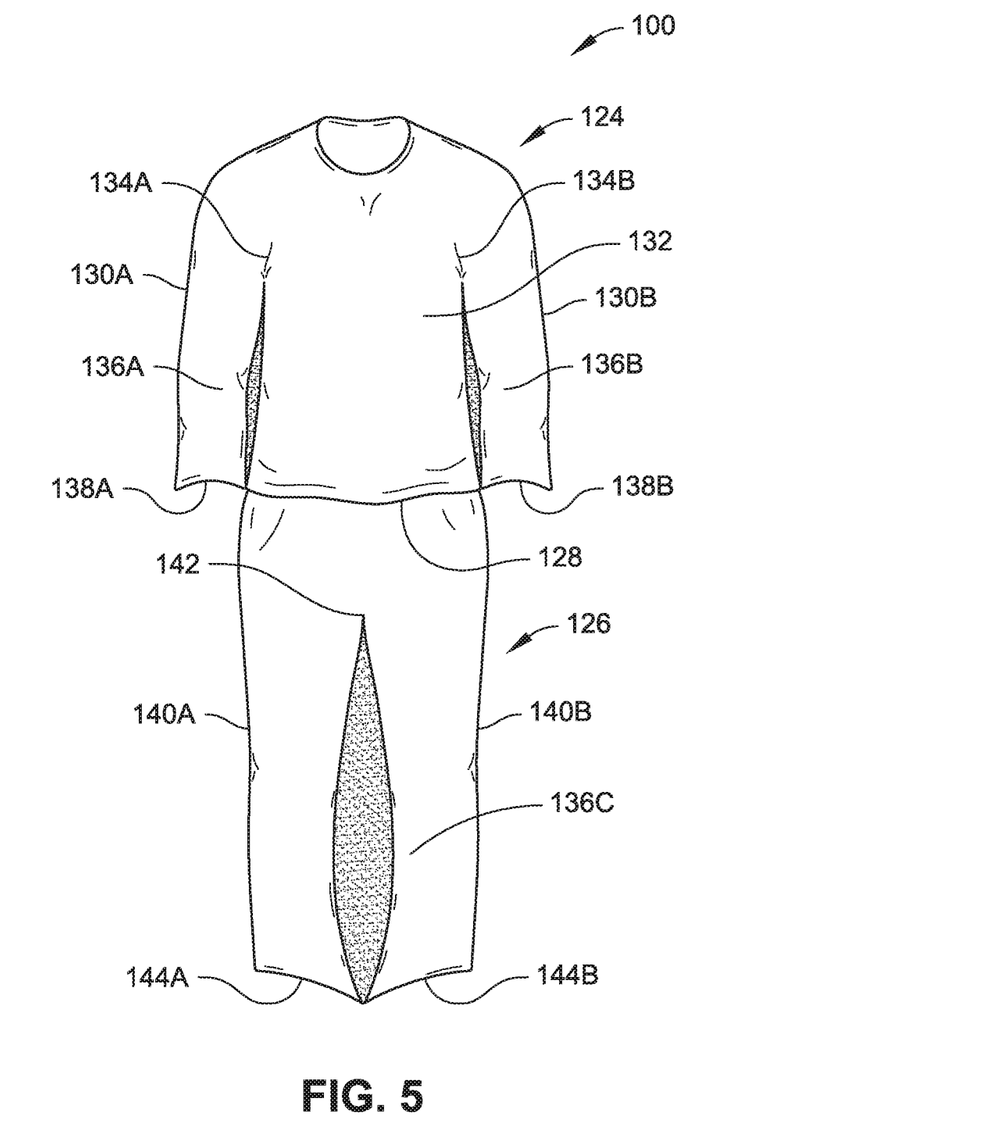
FIG. 5 is a front view illustrating a motion restriction garment including an upper pants portion and a lower jacket portion in accordance with an example embodiment of the present disclosure.

Referring now to FIG. 4, the sleeves 106A, 106B and/or leg portions 108A, 108B can be constructed in varying lengths to accommodate the wearer 102. The length of the sleeves 106A, 106B and/or leg portions 108A, 108B can be selected based on a variety of factors including, but not necessarily limited to: desired level of movement restriction, climate, size/height of the wearer 102, comfortability, and so forth. The overall size of the garment 100 can also vary depending on various factors such as the size of the wearer 102. The circumference of the sleeves 106A, 106B and/or leg portions 108A, 108B can also be selected to accommodate the wearer 102. The circumference of the sleeves 106A, 106B and/or leg portions 108A, 108B can be selected based on a variety of factors including, but not necessarily limited to: desired level of movement restriction, climate, size/height of the wearer 102, comfortability, and so forth. In specific embodiments, the sleeves 106A, and 106B restrict a wearer's range of motion to about 35 degrees abduction (e.g., movement from the wearer's and/or garment's midline) or less, and the leg portions 108A, 108B restrict a wearer's range of motion to about 30 degrees abduction, or less. The leg portions 108A, 108B can also restrain a wearer's leg movement to approximately the width of the wearer's shoulders and/or the width of the shoulder portions of the garment.

In some embodiments, the garment 100 can be constructed as a one-piece garment (e.g., as described with reference to FIGS. 2A and 2B). In other embodiments, the garment 100 can be constructed as a two-piece garment including an upper jacket portion 124 and a lower pants portion 126 (e.g., as described with reference to FIG. 5). For example, the body assembly 104 can include one or more garment forming portions configured to form the upper jacket portion 124 and the lower pants portion 126. The upper jacket portion 124 and the lower pants portion 126 can be fixedly or removably coupled at a waist 128. In some embodiments, the upper jacket portion 124 can be removably coupled with the lower pants portion 126 by one or more fasteners. Suitable fasteners can include, but are not necessarily limited to: zippers, a fastener material (e.g., Velcro® available from Velcro Companies, London, UK), buttons, snaps, buckles, other similar fasteners, and so forth. In a specific embodiment, the fastener can include a zipper configured to extend about the waist circumference of the garment 100. For example, a female end of the zipper can be coupled to the upper jacket portion 124 and configured to mate with a corresponding male end coupled to the lower pants portion 126. However, this configuration is offered by way of example only and is not meant to be restrictive of the present disclosure. In other embodiments, the upper jacket portion 124 can be removably coupled to the lower pants portion 126 by other types of fasteners, or can be fixedly coupled to the lower pants portion 126 by a fixed attachment device such as a seam. It is also contemplated that the upper jacket portion 124 can be integral to the lower pants portion 126, forming a one-piece garment.

The upper jacket 124 portion can include a first sleeve and a second sleeve 130A, 130B coupled to a torso area 132 at first and second armpit areas 134A, 134B, respectively. In some embodiments, the sleeves 130A, 130B can be coupled with the torso area 132 to restrict the range of motion of the wearer 102. The sleeves 130A, 130B can be coupled to the torso area 132 using any of the techniques described above (e.g., as described with reference to FIGS. 2A through 3). For example, the sleeves 130A, 130B can be secured to the torso area 132 by a first attachment device 136A and a second attachment device 136B, respectively, configured to extend vertically from the respective armpit area 134A, 134B toward a distal end 138A, 138B of the respective sleeve 130A, 130B.

The lower pants portion 126 can include a first leg portion 140A and a second leg portion 140B coupled to the waist 128. In some embodiments, the first leg portion 140A can be joined to the second leg portion 140B to restrict the range of motion of the wearer 102. The first leg portion 140A can be coupled to the second leg portion 140B using any of the techniques described above (e.g., as described with reference to FIGS. 2A through 3). For example, the first leg portion 140A can be joined to the second leg portion 140B by an attachment device 136C configured to extend vertically from an inseam 142 of the lower pants portion 126 and toward a distal end 144A, 144B of the first and second leg portions 140A, 140B.

Figure 6:
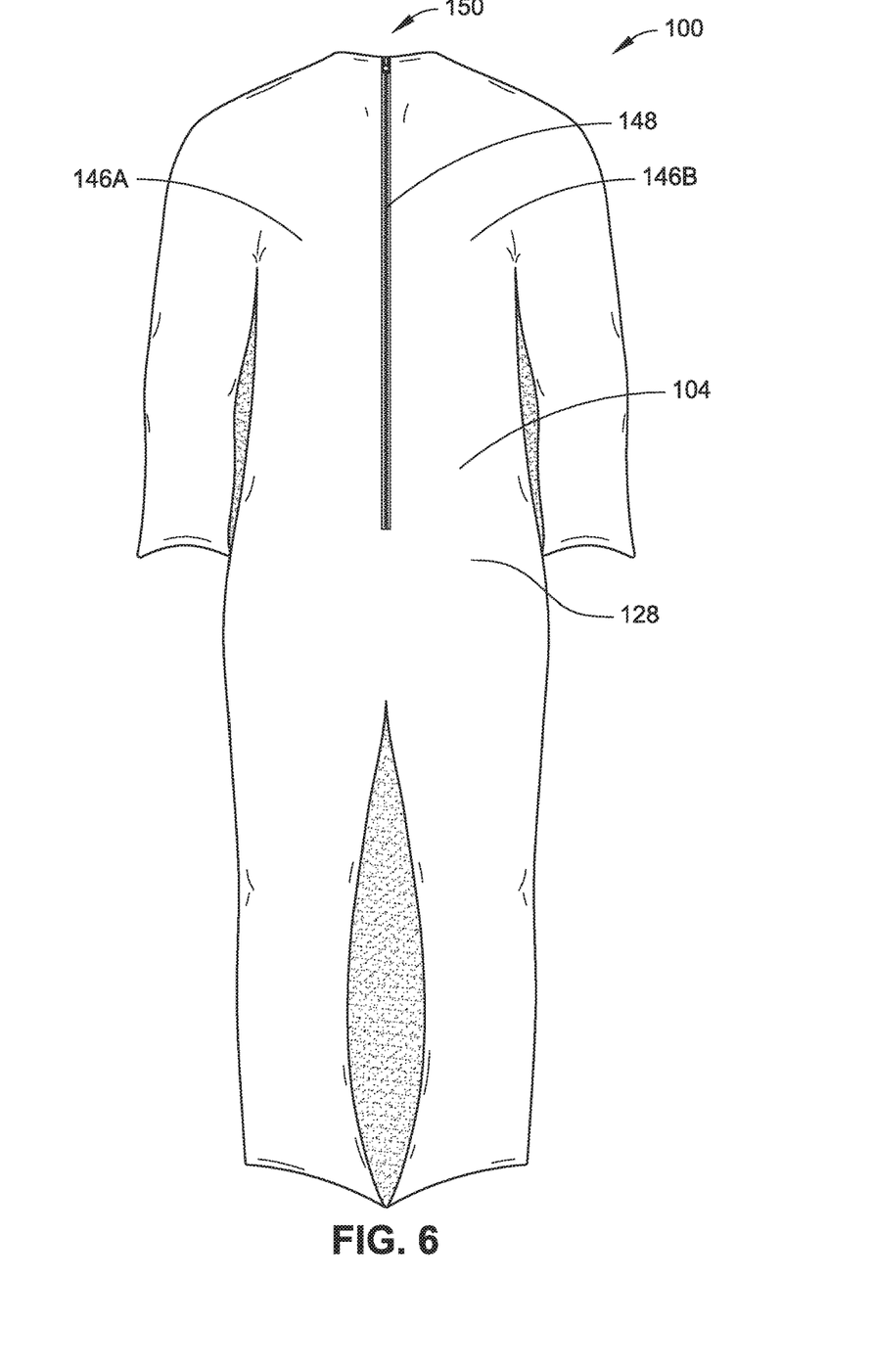
FIG. 6 is a back view illustrating a motion restriction garment including a fastener in accordance with an example embodiment of the present disclosure.

Referring now to FIG. 6, the garment 100 can include a fastener to assist the wearer 102 in donning or removing the garment 100. For example, the body assembly 104 can include a first side 146A and a second side 146B configured to be removably joined by one or more fasteners. Suitable fasteners can include, but are not necessarily limited to: zippers, a fastener material (e.g., Velcro® available from Velcro Companies, London, UK), buttons, snaps, buckles, other similar fasteners, any combination thereof, and so forth. In some embodiments, the fastener can include a zipper 148 that can extend vertically from an upper area of the garment 100 toward a lower portion of the garment 100. For example, the zipper 148 can extend from a neck area 150 (e.g., collar area) of the body assembly 104 towards the waist area 128, or from the neck area of the upper jacket portion 124 towards the lower pants portion 126. In a specific embodiment, the zipper 148 is centrally positioned on a back side of the garment 100 (e.g., on the wearer's 102 back). This positioning helps prevent the wearer 102 from self-removing the garment 100, given the restricted range of motion of the user's hands and arms. In other embodiments, the garment 100 can include a plurality of fasteners configured to extend vertically from the neck area of the garment 100 towards a lower portion of the garment 100. For example, the garment 100 may be secured by a plurality of ties or buckles.

It is to be understood that, while the fastener is shown disposed on the upper back side of the garment 100 in FIG. 6, the fastener can be positioned at various locations on the garment 100 (e.g., front of garment 100, on the sides of the garment 100, along the inner surface of the leg portions 108A, 108B, etc.). The positioning of the fastener can be based on factors such as the desired level of access for the wearer 102, desired level of restraint, desired level of security, and so forth. For example, for wearers 102 requiring a low level of security, front or side fasteners can be utilized that may allow the wearer 102 to don or remove the garment 100 without assistance.

Figure 7A:
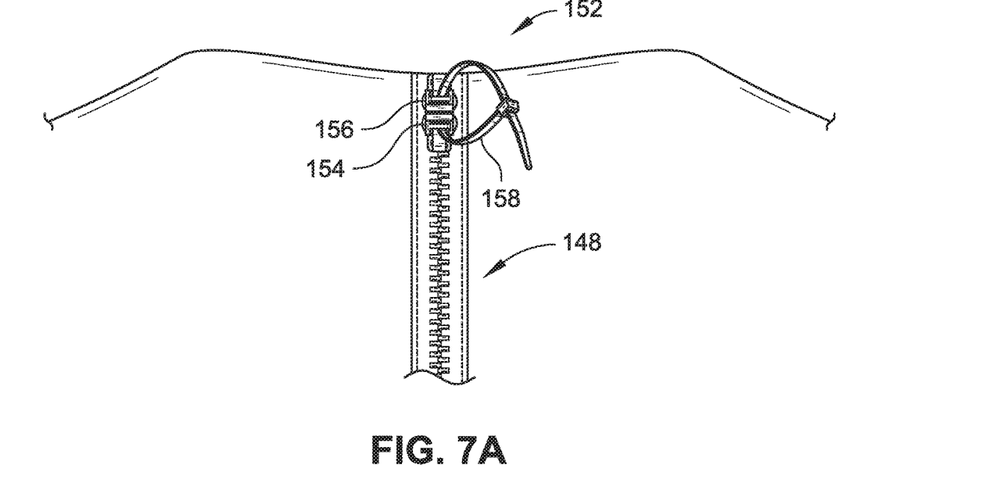
FIG. 7A is a front view illustrating a fastener of a motion restriction garment, such as the motion restriction garment illustrated in FIG. 6, in accordance with an example embodiment of the present disclosure.
Figure 7B:
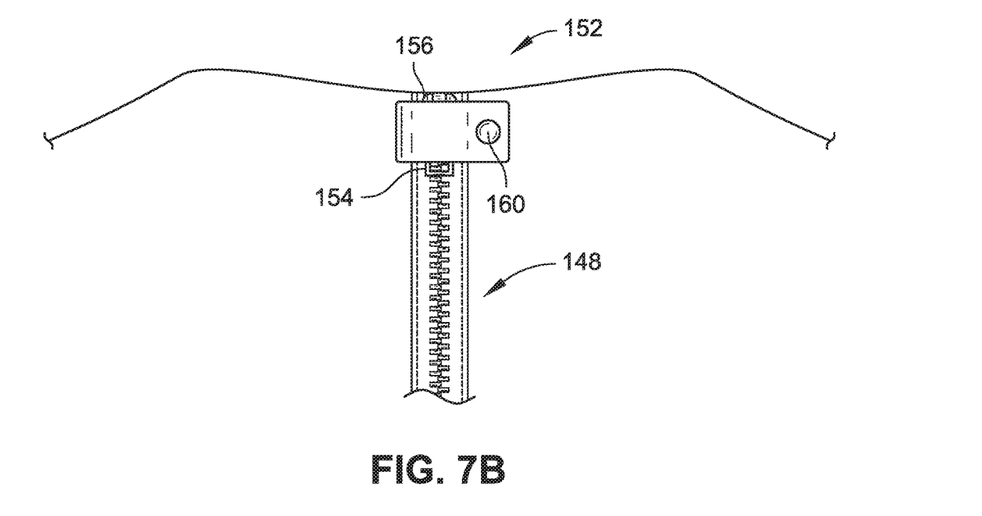
FIG. 7B is another front view illustrating a fastener of a motion restriction garment, such as the motion restriction garment illustrated in FIG. 6, in accordance with an example embodiment of the present disclosure.

Referring now to FIGS. 7A and 7B, the fastener can further include a locking device (e.g., snap, button, zip-tie, etc.) configured to retain the fastener in a selected orientation. In specific embodiments, zipper 148 can include a locking device configured to retain the zipper 148 in a zipped orientation. For example, the zipper 148 can include a locking device 152 configured to couple a slider 154 of the zipper 148 with a zipper stop 156 (e.g., as described with reference to FIG. 7A). Suitable locking devices can include any fastener configured to couple the slider 154 with the zipper stop 156 including, but not necessarily limited to: zip-ties (e.g., zip-tie 158), straps, ties, clips, hooks, and so forth. In other embodiments, the zipper 148 can include a locking device 152 configured to cover the slider 154 and the zipper stop 156 when the zipper 148 is in the zipped orientation (e.g., when the slider 154 is adjacent to the zipper stop 156; as described with reference to FIG. 7B). For example, the locking device 152 can include a flap of textile material configured to cover the slider 154 and the zipper stop 156 when the zipper 148 is in the zipped orientation. The locking device 152 can further include a fastener 160 configured to retain the flap of textile material in closed orientation. Suitable fasteners include, but are not necessarily limited to: buttons, snaps, buckles, other similar fasteners, and so forth. The locking device 152 can reduce the wearer's 102 ability to remove the garment without assistance. The restrained nature of the wearer's 102 arms also reduces the wearer's 102 ability to reach the fastener and/or the locking device, further reducing the wearer's 102 ability to remove the garment 100 without assistance.

Figure 8:
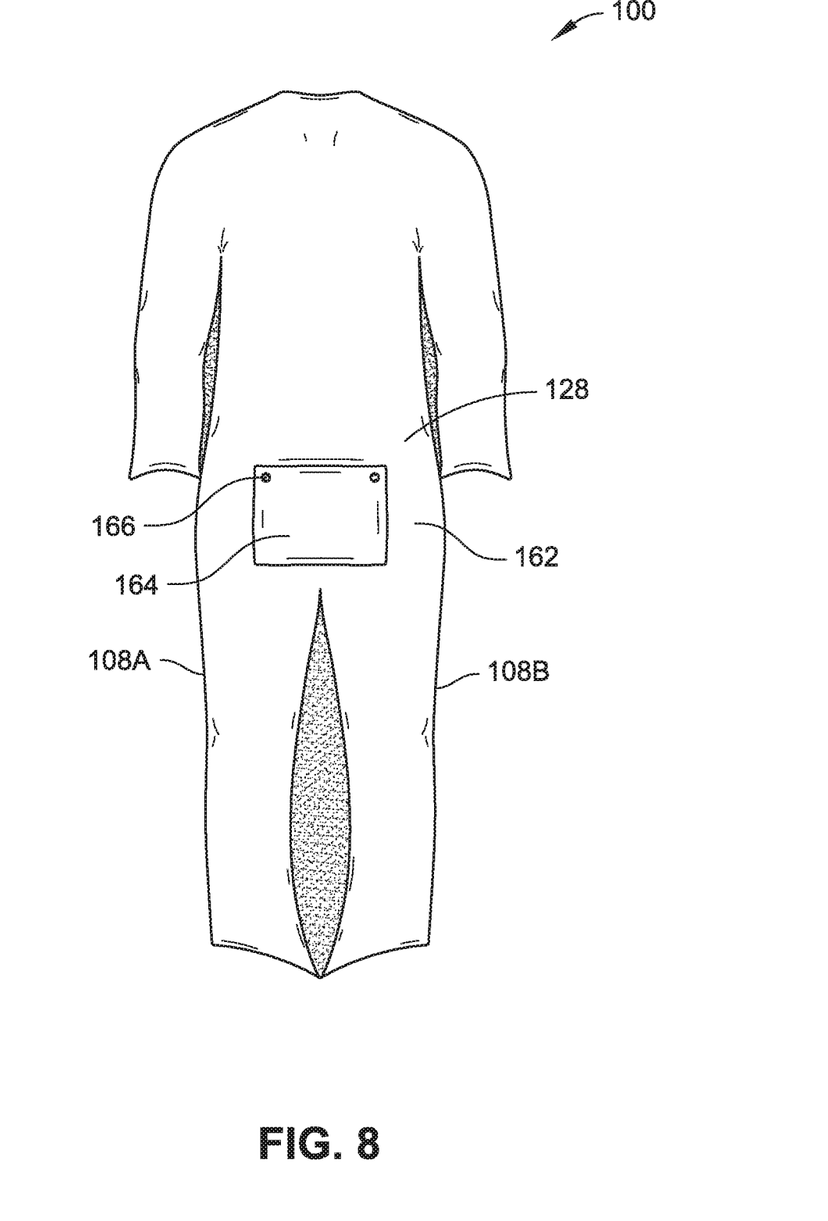
FIG. 8 is a back view illustrating a motion restriction garment including a drop seat in accordance with an example embodiment of the present disclosure

Referring now to FIG. 8, the garment 100 can further include a drop seat 162 disposed on the back side of the garment 100 on the lower portion of the garment 100 (e.g., below the waist area 128). The drop seat 162 includes a flap 164 that is integral with one section of the garment 100 and removably secured to the other section of the garment 100 by one or more fasteners 166. The positioning of the fasteners 166 can be selected based on proximity to the wearer's 102 hands given the wearer's 102 restricted range of motion. In a specific embodiment, the fasteners 166 can be disposed on the upper portion of the flap 164 in close proximity to the wearer's 102 hands. This configuration permits the wearer 102 to reach the fasteners 166 without assistance, but without providing the ability to reach the zipper 148 or the leg portions 108A, 108B. While the drop seat 162 is shown on a one-piece garment 100 in FIG. 8, it is contemplated that a drop seat 162 can also be included on a two-piece garment, such as the garment shown in FIG. 5.

In embodiments, the garment 100 can include additional measures of coverage and/or restraint. In some embodiments, the garment 100 is configured to enclose the hands and/or the feet of the wearer 102. For example, the sleeves 106A, 106B can include gloves coupled at or near the distal end of the sleeves 106A, 106B (e.g., at the cuffs). Similarly, the garment 100 can include foot portions (e.g., socks) coupled to the distal end of the leg portions 108A, 108B (e.g., at the cuffs) and configured to enclose the feet of the wearer 102. In other embodiments, the sleeves 106A, 106B and/or the leg portions 108A, 108B can also be configured as enclosed sleeves and/or leg portions. For example, the sleeves 106A, 106B and/or leg portions 108A, 108B can be fixedly or removably closed at the distal end by one or more attachment devices. Suitable attachment devices can include, but are not necessarily limited to: seams, zippers, a fastener material (e.g., Velcro® available from Velcro Companies, London, UK), buttons, snaps, buckles, other similar fasteners, and so forth. In some embodiments, the attachment device can include a locking device allowing the fastener to be retained in a desired orientation utilizing any of the techniques described above. In some embodiments, the garment can be configured to enclose the head and/or face of the wearer 102. For example, the garment 100 can include a hood configured to be fixedly or removably attached to an upper portion of the garment 100 (e.g., at the neck or collar area).

In embodiments, the motion restriction garment 100 can be formed from a variety of textile materials including, but not necessarily limited to: twill, cotton, polyester, cotton-polyester blends, nylon, reinforced nylon (e.g., Ripstop nylon), canvas, duck fabric (e.g., Cordura® Duck fabric available from Invista, Wichita, Kans.), aramid and/or para-aramid fibers (e.g., Kevlar® available from DowDuPont, Midland, Mich.), other synthetic fibers or synthetic fiber blends, other natural fibers or natural fiber blends, combinations thereof, and so forth. In embodiments, the textile material can be selected based on a variety of factors including, but not necessarily limited to: strength (e.g., tear strength, tensile strength, etc.), weight, durability, flexibility, climate, and so forth. In some embodiments, the textile material can be an industrial grade or heavy-duty textile material. For example, the textile material can have a tear strength of at least 15 N, and/or a tensile strength of at least 400 N. In a specific embodiment, the textile material has a tear strength in the range of approximately 15 N to approximately 140 N, and/or a tensile strength in the range of approximately 400 N to approximately 1800 N. In some embodiments, the body assembly 104 and the sections of textile material 122A, 122B, 122C can be formed from the same textile material. In other embodiments, the sections of textile material 122A, 122B, 122C can be formed from a different textile material than other areas of the garment 100. For example, a stronger textile material (e.g., greater tear strength and/or tensile strength) can be utilized for the sections of textile material 122A, 122B, 122C. Using a stronger textile material at these positions can help increase the durability of the garment and reduce tearing at critical locations. The sections of textile material 122A, 122B, 122C may also be formed from a material having a greater elasticity than the than the material used on other areas of the garment. Utilizing a material with elasticity for the sections of textile material 122A, 122B, 122C can provide an increased, while still restricted, range of motion. The stitching type and/or thread type can also be selected to increase the durability of the garment 100 and reduce tearing. In a specific embodiment, triple needle stitching is utilized.

It is to be understood that while some features included herein are shown only on a one-piece garment, those features can also be included on a two-piece garment. It is to be further understood that while the garments 100 illustrated in FIGS. 1-6 and 8 are configured to restrict both the legs and the arms of the wearer 102, the same techniques may be utilized to restrict only the arms, only the legs, or a combination thereof. The level of restraint selected (e.g., arms only, legs only, both arms and legs, etc.) can be based on a variety of factors including, but not necessarily limited to: desired level of security for the wearer 102, tendencies of the wearer 102 (e.g., level of violence, physical ability, etc.), security level of the facility, and so forth. It is further contemplated that the garment 100 can be utilized in conjunction with other restraint devices (e.g., handcuffs, shackles, etc.) to achieve a greater level of restraint.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A garment for restricting the range of motion of a wearer, comprising:
    a body assembly, the body assembly including one or more garment forming portions configured to form a first side and a second side, the first side and the second side configured to be removably joined by at least one fastener;
    a first sleeve and a second sleeve coupled to the body assembly at a first armpit area and a second armpit area, respectively, each of the first sleeve and the second sleeve being securely attached to the body assembly by a first attachment device and a second attachment device, respectively, each of the first attachment device and the second attachment device extending vertically from the respective armpit area toward a distal end of the respective sleeve, wherein the first attachment device is a first seam that non-releasably and directly couples at least one half of the first sleeve to a torso area of the body assembly so that the first sleeve fixedly restricts a first arm range of motion to a range of 35 degrees abduction or less, and wherein the second attachment device is a second seam that non-releasably and directly couples at least one half of the second sleeve to the torso area of the body assembly so that the second sleeve fixedly restricts a second arm range of motion to a range of 35 degrees abduction or less; and
    a first leg portion and a second leg portion, each of the first leg portion and the second leg portion coupled to the body assembly at an inseam, the first leg portion and the second leg portion being joined by a third attachment device extending vertically from the inseam toward a distal end of the first leg portion and the second leg portion, wherein the third attachment device is a third seam that non-releasably and directly couples at least one half of the first leg portion to the second leg portion so that the first leg portion fixedly restricts a first leg range of motion to a range of 30 degrees abduction or less and so that the second leg portion fixedly restricts a second leg range of motion to a range of 30 degrees abduction or less.

2. The garment as recited in claim 1, wherein the at least one fastener comprises a zipper configured to extend vertically from a neck area of the body assembly to a waist area of the body assembly.

3. The garment as recited in claim 2 wherein the zipper is configured to lock in a zipped orientation.

4. The garment as recited in claim 1, wherein the garment is formed from a textile material having a tear strength of at least 15 N.

5. A garment for restricting the range of motion of a wearer, comprising:
    a body assembly, the body assembly including one or more garment forming portions configured to form an upper jacket portion and a lower pants portion coupled at a waist;
    a first sleeve coupled to the body assembly at a first armpit area, the first sleeve being securely attached to the body assembly by a first attachment device extending vertically from the first armpit area toward a distal end of the first sleeve, wherein the first attachment device is a first seam that non-releasably and directly couples at least one half of the first sleeve to a torso area of the body assembly so that the first sleeve fixedly restricts a first arm range of motion to a range of 35 degrees abduction or less;
    a second sleeve coupled to the body assembly at a second armpit area, the second sleeve being securely attached to the body assembly by a second attachment device extending vertically from the second armpit area toward a distal end of the second sleeve, wherein the second attachment device is a second seam that non-releasably and directly couples at least one half of the second sleeve to the torso area of the body assembly so that the second sleeve fixedly restricts a second arm range of motion to a range of 35 degrees abduction or less;
    a first leg portion and a second leg portion, each of the first leg portion and the second leg portion coupled to the body assembly at an inseam, the first leg portion and the second leg portion being joined by a third attachment device extending vertically from the inseam toward a distal end of the first leg portion and the second leg portion, wherein the third attachment device is a third seam that non-releasably and directly couples at least one half of the first leg portion to the second leg portion so that the first leg portion fixedly restricts a first leg range of motion to a range of 30 degrees abduction or less and so that the second leg portion fixedly restricts a second leg range of motion to a range of 30 degrees abduction or less; and
    at least one fastener configured to extend from a neck area of the upper jacket portion to a portion of the lower pants portion.

6. The garment as recited in claim 5, wherein the garment is formed from a textile material having a tear strength of at least 15 N.

7. The garment as recited in claim 5, wherein the at least one fastener comprises a zipper.

8. The garment as recited in claim 7, wherein the zipper is configured to lock in a zipped orientation.

* * * * *